United States Patent [19]

Francese et al.

[11] Patent Number: 4,788,012

[45] Date of Patent: Nov. 29, 1988

[54] PROCESS FOR THE PREPARATION OF BENZYL TRIFLUOROMETHYL SULFIDE

[75] Inventors: Catherine Francese, L'Hay les Roses; Marc Tordeux, Sceaux; Claude Wakselman, Paris, all of France

[73] Assignee: Rhone-Poulenc Chimie, Cedex, France

[21] Appl. No.: 52,074

[22] Filed: May 21, 1987

[30] Foreign Application Priority Data

May 28, 1986 [FR] France ................................ 86 07854

[51] Int. Cl.$^4$ ................. C07C 143/70; C07C 149/273
[52] U.S. Cl. ................................. 260/543 R; 558/425; 568/51; 568/52; 568/56
[58] Field of Search ...................... 568/51, 52, 56, 639, 568/655; 260/543 R; 570/185; 558/425

[56] References Cited

U.S. PATENT DOCUMENTS 3,226,433 12/1965 Bennett et al. .................. 260/543 R
3,282,979 11/1966 Reifschneider et al. ............. 568/52
3,506,718  4/1970 Mutsch ................................ 568/56

FOREIGN PATENT DOCUMENTS 849061 9/1960 United Kingdom .

OTHER PUBLICATIONS

E. Lewis et al, J. Am. Chem. Soc. 1985, 107, 6668–6673.
T. Nguyen et al, J. Org. Chem. 1981, 46, 1938–1940, Reaction of Perfluoroalkyl Carbanions with Thiocyanates. Synthesis of Fluorinated Sulfides and Sulfenyl Chlorides.

Primary Examiner—Mary E. Ceperley
Attorney, Agent, or Firm—Finnegan, Henderson, Farabow, Garrett, & Dunner

[57] ABSTRACT

A process for the preparation of a benzyl trifluoromethyl sulfide by bringing a benzyl thiocyanate and trifluoromethyl bromide into contact with zinc in a polar aprotic solvent or a pyridine. The invention also relates to a process for the preparation of trifluoromethane sulfonyl chloride by bringing a benzyl trifluoromethyl sulfide into contact with chlorine and water.

12 Claims, No Drawings

PROCESS FOR THE PREPARATION OF BENZYL TRIFLUOROMETHYL SULFIDE

The present invention relates to a new process for the preparation of a benzyl trifluoromethyl sulfide. It also relates to a process for the preparation of trifluoromethane sulfonyl chloride in two stages, wherein the second stage involves conversion of a benzyl trifluoromethyl sulfide intermediate to trifluoromethane sulfonyl chloride.

A few processes are currently known for the preparation of benzyl trifluoromethyl sulfide. Lewis, MacLaughlin, Douglas (J. Am. Chem. Soc. 1985, 107, 6668–6673) discloses a process for the preparation of benzyl trifluoromethyl sulfide which consists of bringing trifluoromethyl iodide into contact with a benzyl mercaptan in liquid ammonia in the presence of radiation. This process can be used on a laboratory scale but is not believed to be suitable for use on an industrial scale.

Nguyen, Rubinstein, Wakselman (J. Org. Chem. 1981, 46, 1938) discloses a process for the preparation of perfluoroalkylated sulfides by reacting a perfluoroalkylated Grignard reagent of the general formula $R_FM_gX$, in which RF denotes a perfluoroalkyl radical and X denotes a halogen, with a benzyl thiocyanate in ethyl ether at a temperature of $-20°$ C. This reaction cannot be utilized on an industrial scale to manufacture perfluoromethylated derivatives since perfluoromethylated Grignard reagents are not available on the market.

The present invention provides a process, suitable for use on an industrial scale, for the preparation of a benzyl trifluoromethyl sulfide from raw materials available on the industrial market. The invention also makes it possible to convert the benzyl trifluoromethyl sulfide obtained into trifluoromethane sulfonyl chloride, a product with high market demand.

The present invention relates to a process for the preparation of a benzyl trifluoromethyl sulfide comprising contacting a benzyl thiocyanate and trifluoromethyl bromide with zinc in the presence of a polar aprotic solvent, pyridine or substituted pyridine for a time sufficient to form the benzyl trifluoromethyl sulfide.

Within the meaning of the present invention, preferred "benzyl trifluoromethyl sulfides" are compounds of the general formula (I):

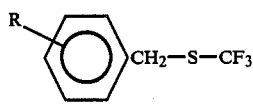
(I)

in which R represents a radical selected from the group consisting of hydrogen, alkyl, alkoxy, alkylthio, aryl, aryloxy, arylthio, halo and cyano.

According to the invention, the preparation of unsubstituted benzyl trifluoromethyl sulfide is preferred.

The benzyl thiocyanates useful in the process of this invention are preferably of the general formula (II):

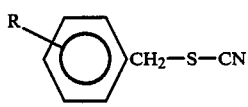
(II)

in which R has the same meaning as in formula (I).

Unsubstituted benzyl thiocyanate is preferably used as the raw material since it is readily available on the market, is economical, and can be easily prepared by reacting sodium or potassium thiocyanate with, for example, benzyl bromide or chloride.

The zinc is preferably used in the dispersed form so as to ensure the best possible contact with the trifluoromethyl bromide gas employed in the process. In practice, the particle size and shape of the metal can readily be selected by one of ordinary skill in the art according to the reactivity of the products employed.

Benzyl thiocyanate and trifluoromethyl bromide should preferably be soluble in the solvent chosen. The following optionally substituted pyridines and polar aprotic solvents meet this condition and are preferred:

acetonitrile
dimethylformamide (D.M.F.)
dimethylacetamide (D.M.A.)
hexamethylphosphoramide (H.M.P.A.)
dimethyl sulfoxide (D.M.S.O.)
N-methylpyrrolidone (N.M.P.)

Pyridine and dimethylformamide are the preferred solvents.

According to a preferred embodiment of the invention, a molar ratio of zinc to the benzyl thiocyanate greater than or equal to 1:1 and a molar ratio of trifluoromethyl bromide to the benzyl thiocyanate greater than or equal to 1:1 are used. If an excess of trifluoromethyl bromide is used, it can easily be recycled since it is in the gaseous form. To increase the solubility of the gas in the reaction medium, it is preferable to operate at a trifluoromethyl bromide pressure ranging from 1 to 50 bar.

The reaction is preferably carried out in the absence of oxygen.

The reaction temperature may vary within wide limits. However, a temperature ranging from $0°$ to $100°$ C. is preferred.

The quantity of solvent used is not critical for implementing the reaction. In practice, it will simply be selected according to the solubility of the starting product.

The products resulting from the present invention can be separated by extraction with organic solvents, washing with water, drying and distillation. Such separation processes are well-known to those of ordinary skill in the art.

The present invention also relates to the preparation of trifluoromethane sulfonyl chloride.

The benzyl trifluoromethyl sulfide obtained may be converted into trifluoromethane sulfonyl chloride by "oxidative chlorination." The term "oxidative chlorination," which refers to the joint action of chlorine and water, can be exemplified by the following chemical reaction:

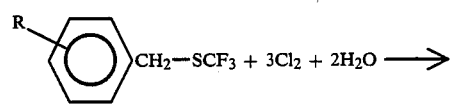

wherein R is as defined above in formulae (I) and (II).

The reaction is preferably carried out at a temperature ranging from 0° to 30° C. in the presence of at least a stoichiometric quantity of chlorine. The reaction is preferably carried out using a chlorine pressure ranging from 1 to 10 bar.

The trifluoromethane sulfonyl chloride is easily recovered from the reaction medium by decantation, carried out at a temperature of from −15° to 10° C. Decantation procedures are wellknown to one of ordinary skill in the art.

Benzyl chloride, which is a by-product of the reaction, can be recycled and used as raw material during the synthesis of benzyl thiocyanate.

The desired products of the process of the invention are especially useful as intermediates in the pharmaceutical or the plant protection industries. See Japanese Patent Publication 58 128 343.

The invention will be described more completely using the following examples which must not be regarded as limiting the invention.

EXAMPLE

1st Staqe 25 ml of pyridine, 8 g (0.0537 mol) of benzyl thiocyanate and 4 g (0.0615 mol) of zinc powder were placed in a round-bottomed flask. The flask was purged with nitrogen and a stream of bromotrifluoromethane was passed through while stirring the solution. The reaction is exothermic.

The mixture was filtered and the filtrate was hydrolyzed with 20 ml of ice cold 10% hydrochloric acid for approximately 30 minutes while stirring. After extracting with ether, washing with water, drying over magnesium sulfate and removing the solvent, the benzyl trifluoromethyl sulfide was distilled under vacuum to yield the following:

b.p.: 54°–56° C./11 mm/Hg. Weight of product: 2.3 g (yield 22% based on benzyl thiocyanate.)

(b.p. lit: 76°–77° C./30 mm/Hg.) $19_F\ NMR\ (CFCl_3\ ext.)$: −41.3 ppm. $1_H$ NMR (TMS int.), 7.3 ppm (m, $C_6H_5$), 4.1 ppm (s, $CH_2$).

2nd Stage

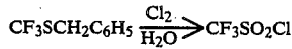

1.6 g (0.0083 mol) of benzyl trifluoromethyl sulfide and 10 ml of distilled water were placed in a thick round-bottomed flask.

The flask was placed in a Parr bomb. A vacuum was created therein and chlorine gas was introduced until a pressure of 4 bar was obtained. The contents were stirred for 2 hours, the temperature being maintained between 0° and 10° C.

The crude reaction mixture was then decanted in the cold state and the lower phase was collected. Trifluoromethane sulfonyl chloride was isolated with 70% yield and the following:

b.p.: 29°–32° C./760 mm/Hg,
$19_F$ NMR ($CFCl_3$ ext.): −74 ppm.

When the second stage was carried out in the absence of water and by replacing the water with 10 ml of 1,1,2,2,-tetrachloroethane, chlorotrifluoromethyl sulfide was obtained with a yield of 62% (b.p.: 1° C.)

We claim:

1. A process for the preparation of a benzyl trifluoromethyl sulfide comprising contacting a benzyl thiocyanate and trifluoromethyl bromide with zinc in a solvent selected from the group consisting of a polar aprotic solvent, substituted pyridine and pyridine for a time sufficient to form said benzyl trifluoromethyl sulfide.

2. The process of claim 1, wherein said benzyl thiocyanate is of the formula (II):

$$R-\underset{}{\underset{}{\bigcirc}}-CH_2-SCN \qquad (II)$$

in which R represents a radical selected from the group consisting of hydrogen, alkyl, alkoxy, alkylthio, aryl, aryloxy, arylthio, halo and cyano.

3. The process of claim 2, wherein R represents hydrogen.

4. The process of claim 1, wherein said polar aprotic solvent is selected from the group consisting of dimethylformamide, dimethyl sulfoxide, acetonitrile, hexamethylphosphoramide, dimethylacetamide and N-methylpyrrolidone.

5. The process of claim 4, wherein said polar aprotic solvent is dimethylformamide.

6. The process of claim 1, wherein said solvent is pyridine.

7. The process of claim 1, wherein the molar ratio of zinc to said benzyl thiocyanate is greater than or equal to 1:1.

8. The process of claim 1, wherein the molar ratio of trifluoromethyl bromide to said benzyl thiocyanate is greater than or equal to 1:1.

9. The process of claim 1, wherein the reaction is carried out at a temperature ranging from 0° to 100° C.

10. The process of claim 1, wherein the reaction is carried out at a pressure ranging from atmospheric pressure to 50 bar.

11. A process for the preparation of trifluoromethane sulfonyl chloride comprising:
(1) contacting a benzyl thiocyanate and trifluoromethyl bromide with zinc in a solvent selected from the group consisting of a polar aprotic solvent, substituted pyridine and pyridine for a time sufficient to form a benzyl trifluoromethyl sulfide, and
(2) contacting the benzyl trifluoromethyl sulfide resulting from stage (1) with chlorine in water for a time sufficient to form trifluoromethane sulfonyl chloride.

12. The process of claim 11, wherein a chlorine pressure ranging from 1 to 10 bar is employed in stage (2).

* * * * *